US00PP16342P3

(12) United States Plant Patent
Meilland

(10) Patent No.: US PP16,342 P3
(45) Date of Patent: Mar. 14, 2006

(54) FLORIBUNDA ROSE PLANT NAMED 'MEIPOMOLO'

(50) Latin Name: *Rosa hybrida*
Varietal Denomination: Meipomolo

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 72 days.

(21) Appl. No.: 10/832,325

(22) Filed: Apr. 27, 2004

(65) Prior Publication Data

US 2005/0177907 P1 Aug. 11, 2005

(30) Foreign Application Priority Data

Feb. 5, 2004 (QZ) ..... PBR 20040167

(51) Int. Cl.
*A01H 5/00* (2006.01)

(52) U.S. Cl. ..... Plt./146
(58) Field of Classification Search ..... Plt./146, Plt./147, 145, 105
See application file for complete search history.

*Primary Examiner*—Anne Marie Grunberg
*Assistant Examiner*—June Hwu
(74) *Attorney, Agent, or Firm*—Burns, Doane, Swecker & Mathis, LLP

(57) ABSTRACT

A new and distinct Floribunda rose plant is provided that forms on a nearly continuous basis attractive bright yellow-orange blossoms. The growth habit is vigorous and bushy. The semi-glossy foliage is dense, dark green and of good substance and contrasts nicely with the yellow-orange blossom coloration. Very good tolerance to Black Spot and Oidium is displayed under normal growing conditions. The plant is well suited for growing as attractive ornamentation in parks and gardens.

1 Drawing Sheet

Figures 1, 2, 3, 4, 5, 6, 7, 8, 9, 10, 11, 12, 13, 14, 15, 16:
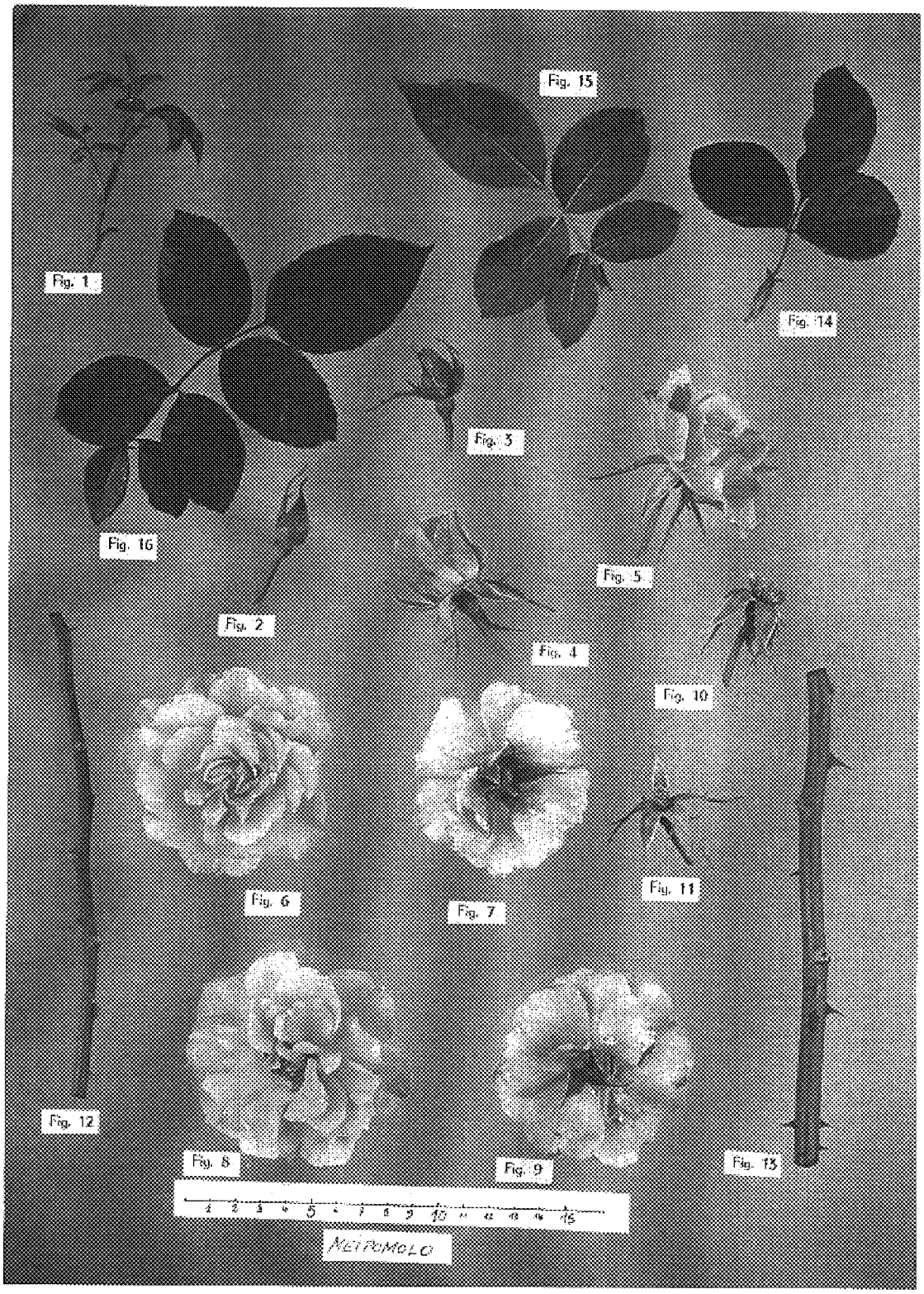

Botanical/commercial classification: *Rosa hybrida*/Floribunda Rose Plant.
Varietal denomination: cv. 'Meipomolo'.

SUMMARY OF THE INVENTION

The new *Rosa hybrida* variety of Floribunda rose plant was created by artificial pollination wherein two parents were crossed which previously had been studied in the hope that they would contribute the desired characteristics. The female parent (i.e., the seed parent) of the new variety was the 'Kortikel' variety (non-patented in the United States). The 'Kortikel' variety sometimes is marketed under the GOLDEN HOLSTEIN trademark. The male parent (i.e., the pollen parent) was the 'Meidomonac' variety (U.S. Plant Pat. No. 5,105). Plants of the 'Meidomonac' variety are marketed under the BONICA trademark. The parentage of the new variety can be summarized as follows:

'Kortikel'×'Meidomonac'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) forms on a nearly continuous basis attractive bright yellow-orange blossoms, (b) exhibits a vigorous and bushy growth habit, (c) forms decorative dense dark green semi-glossy foliage of good substance, (d) displays good tolerance to Oidium and Black Spot, and (e) is well suited for growing as attractive ornamentation in parks and gardens.

The yellow-orange blossom coloration is luminous in character and contrasts nicely with the dark green foliage. Blooming commonly occurs on a substantially uninterrupted basis from May to November. The plant is well suited for growing in U.S.D.A. Hardiness Zone No. 6.

The new variety of the present invention can be readily distinguished from its ancestors. More specifically, the blossoms of the 'Kortibel' variety are pure yellow instead of bright yellow-orange. The 'Meidomonac' variety forms dissimilar medium pink blossoms.

The new variety of the present invention also can be readily distinguished from other similar Floribunda rose varieties, such as the 'Meibaltaz' (U.S. Plant Pat. No. 8,449) and 'Meimonblan' (U.S. Plant Pat. No. 12,579) varieties. Each forms blossoms having a different coloration. The 'Meibaltaz' variety forms yellow blossoms and the 'Meimonblan' variety forms darker tangerine orange blossoms.

The new variety well meets the needs of the horticultural industry and is particularly well suited for enhancing the appearance of the landscape.

The new variety has been found to undergo asexual propagation in France by a number of routes, including budding, grafting, and cuttage. Asexual propagation by the above-mentioned techniques in the South of France has shown that the characteristics of the new variety are stable and are strictly transmissible by such asexual propagation from one generation to another.

The new variety has been named the 'Meipomolo' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during September while budded on *Rosa froebelli* understock and growing outdoors at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during October while budded on *Rosa froebelli* understock and growing outdoors at Le Cannet des Maures, Var, France. Reference to color in common terms is to be accorded its ordinary dictionary significance.

Class: Floribunda.

Plant:

*Height.*—Approximately 80 to 90 cm on average at the end of the growing season.

*Width.*—Approximately 80 to 90 cm on average at the end of the growing season.

*Habit.*—Bushy.

Branches:

*Color.*—Young stems: near Green Group 137A. Adult wood: near Green Group 137B.

*Thorns.*—Configuration: rather upright, longish-pointed on the upper surface and concave on the under surface. On young stems: over a length of 18 cm approximately 5 on average long prickles having lengths over 5 mm that are near Greyed-Purple Group 185D in coloration at the base and near Yellow-Green Group 151D towards the tip. On adult stems: over a length of 19 cm approximately 8 on average long prickles having lengths over 5 mm that are near Greyed-Orange Group 166A in coloration.

Leaves:

*Stipules.*—Adnate, pectinate, approximately 2.5 cm in length, approximately 0.8 cm in width, smooth on the upper surface, tomentose on the under surface, and near Green Group 137C in coloration.

*Petioles.*—Upper surface: rather glandular, and near Green Group 136B in coloration. Under surface: tomentose, and near Green Group 137B and 137C in coloration. Length: approximately 1 to 2 cm on average.

*Rachis.*—Upper surface: rather glandular. Under surface: tomentose.

*Size.*—A five-leaflet leaf including the petiole commonly is approximately 11 cm in length on average and approximately 10.5 cm in width on average.

*Leaflets.*—Number: 3, 5 (most often), and 7. Shape: elliptic with a pointed tip and an obtuse base. Size: terminal leaflets commonly are approximately 7 cm in length on average and approximately 3.5 to 4 cm in width on average. Serration: fine and regular (as illustrated). Texture: smooth, semi-glossy, and of good substance. General appearance: very dense, dark green, and semi-glossy. Color (young foliage): Upper surface: dark green, near Green Group 136A with some anthocyanin coloration of near Greyed-Red Group 178A. Under surface: dark green, near Green Group 137A and suffused with some red anthocyanin coloration. Color (adult foliage): Upper surface: dark green, near Green Group 136A. Under surface: dark green, near Green Group 137A.

Inflorescence:

*Number of flowers.*—Commonly in clusters of 2 to 5 flowers per stem.

*Peduncle.*—Possesses good strength, rigid, very slightly glandular, approximately 2 to 2.5 cm in length on average, and near Green Group 138A in coloration.

*Sepals.*—Upper surface: tomentose and near Yellow-Green Group 148B and 148C in coloration. Under surface: smooth, and near Green Group 137B, 137C, and 137D in coloration. Some small extensions are present (as illustrated). Size: approximately 3 cm in length on average, and approximately 0.9 cm in width at the widest point on average.

*Buds.*—Shape: conical. Size: Medium. Length: approximately 1.5 cm on average. Color upper surface: near Yellow-Orange Group 15B and lightly suffused on the first petal whorls with Orange-Red Group 35A as the calyx breaks. Color under surface: near Yellow-Orange Group 15D and widely suffused with Orange-Red Group 35A as the calyx breaks. Spot at base: none observed.

*Flower.*—Blooming habit: commonly blooms in clusters from May to November on a substantially continuous basis. Shape: cup-shaped. Diameter: approximately 7 to 9 cm on average when fully open. Color (when blooming): Upper surface: bright yellow-orange, near Yellow-Orange Group 15B and 15C. Under surface: near Yellow-Orange Group 15D and Yellow-Orange Group 16D and lightly suffused with Orange-Red Group 35C. Spot at base: none observed. Color stability: very slight fading with advancing maturity. Petal number: approximately 29 on average under normal growing conditions. Petal arrangement: imbricated. Petal configuration:

reflexed tip and an obtuse base. Petal shape: generally oval. Petal size: approximately 3.5 cm in length on average, and approximately 3 cm in width on average. Petal texture: smooth. Petal margin: wavy and somewhat reflexed (as illustrated). Petaloids: very few located at the center, commonly approximately 6 in number on average, generally oval in shape, on the upper surface near Yellow-Orange Group 15B and slightly suffused with Orange-Red Group 35A, and on the under surface near Yellow-Orange Group 15D and widely suffused with some orange-red coloration. Stamen: approximately 110 on average. Anthers: regularly disposed around the styles, approximately 0.2 cm in size on average, and near Greyed-Orange Group 177A in coloration. Filaments: approximately 0.4 cm in length on average, and near Greyed-Orange Group 165in coloration. Pistils: approximately 50 on average. Styles: approximately 0.2 cm in length on average, and near Yellow-Green Group 149C in coloration. Stigmas: approximately 0.1 cm in size on average, and near Yellow Group 13B in coloration. Fragrance: none. Lastingness: approximately 15 days on the plant in a garden setting. Petal drop: the petals commonly detach cleanly before drying. Receptacle: smooth, near Green Group 137B suffused with some red anthocyanin coloration, commonly approximately 0.6 to 0.8 cm in length and approximately 0.6 to 0.8 cm in width on average, and in longitudinal section in the shape of a pitcher. Seeds: ovoid in shape, rough in texture, and approximately 0.5 cm in length.

Development:

*Vegetation.*—Very strong.

*Blooming.*—Nearly continuous.

*Tolerance to diseases.*—Very good with respect to Oidium and Black Spot under normal growing conditions.

*Tolerance to heat and cold.*—Good general resistance.

*Aptitude to bear fruit.*—Medium.

I claim:

1. A new and distinct Floribunda rose plant having the following combination of characteristics:

(a) forms on a nearly continuous basis attractive bright yellow-orange blossoms, (b) exhibits a vigorous and bushy growth habit, (c) forms decorative dense dark semi-glossy foliage of good substance, (d) displays good tolerance to Oidium and Black Spot, and (e) is well suited for growing as ornamentation in parks and gardens;

substantially as illustrated and described.

* * * * *

NETPOMOLO